(12) United States Patent
Baumgartner et al.

(10) Patent No.: US 8,207,652 B2
(45) Date of Patent: Jun. 26, 2012

(54) ULTRASOUND TRANSDUCER WITH IMPROVED ACOUSTIC PERFORMANCE

(75) Inventors: Charles Edward Baumgartner, Niskayuna, NY (US); Jean-Francois Gelly, Mougins (FR); Lowell Smith, Niskayuna, NY (US); Charles G. Woychik, Niskayuna, NY (US); Frederic Lanteri, Le Cannet (FR); Stephen Edwardsen, Revetal (NO); Robert S. Lewandowski, Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 195 days.

(21) Appl. No.: 12/485,226

(22) Filed: Jun. 16, 2009

(65) Prior Publication Data

US 2010/0317972 A1    Dec. 16, 2010

(51) Int. Cl.
*H01L 41/08*    (2006.01)
(52) U.S. Cl. ..................................................... 310/334
(58) Field of Classification Search ........... 310/334–337
See application file for complete search history.

(56) References Cited

U.S. PATENT DOCUMENTS

| | | | | |
|---|---|---|---|---|
| 4,217,684 A | * | 8/1980 | Brisken et al. | 29/25.35 |
| 5,329,498 A | * | 7/1994 | Greenstein | 367/155 |
| 5,493,541 A | * | 2/1996 | Snyder | 367/155 |
| 5,629,578 A | * | 5/1997 | Winzer et al. | 310/334 |
| 5,744,898 A | * | 4/1998 | Smith et al. | 310/334 |
| 6,087,762 A | * | 7/2000 | Corbett et al. | 310/334 |
| 6,236,144 B1 | * | 5/2001 | Millar et al. | 310/334 |
| 7,441,321 B2 | | 10/2008 | Baumgartner et al. | |
| 7,821,180 B2 | * | 10/2010 | Kunkel, III | 310/322 |
| 2005/0165313 A1 | | 7/2005 | Byron et al. | |
| 2005/0203409 A1 | | 9/2005 | Frey et al. | |
| 2006/0116584 A1 | | 6/2006 | Sudol et al. | |
| 2008/0129152 A1 | | 6/2008 | Nye et al. | |

FOREIGN PATENT DOCUMENTS

WO    2006075283 A2    7/2006

OTHER PUBLICATIONS

Smith et al., "Two-Dimensional Array Transducers Using Thick Film Connection Technology," IEEE Transactions on Ultrasonics, Ferroelectrics, and Frequency Control, vol. 40, No. 6, Nov. 1993, pp. 727-734.

Wygant et al., "Integration of 2D CMUT Arrays with Front-End Electronics for Volumetric Ultrasound Imaging," IEEE Transactions on Ultrasonics, Ferroelectrics, and Frequency Control, vol. 55, No. 2, Feb. 2008 pp. 327-342.

* cited by examiner

*Primary Examiner* — Mark Budd
(74) *Attorney, Agent, or Firm* — Marie-Claire Maple (57) ABSTRACT

A system for improving the acoustic performance of an ultrasound transducer by reducing artifacts within the acoustic spectrum is disclosed. The system includes an acoustic layer having an array of acoustic elements, a dematching layer coupled to the acoustic layer and having an acoustic impedance greater than an acoustic impedance of the acoustic layer, and an interposer layer coupled to the dematching layer and comprising a substrate and a plurality of conductive element. The interposer layer is formed to have an acoustic impedance lower than the acoustic impedance of the dematching layer. The ultrasound transducer also includes an integrated circuit coupled to the interposer layer and electrically connected to the array of acoustic elements through the dematching layer and the interposer layer.

25 Claims, 6 Drawing Sheets

ULTRASOUND TRANSDUCER WITH IMPROVED ACOUSTIC PERFORMANCE

BACKGROUND OF THE INVENTION

The invention relates generally to ultrasound transducers and, more particularly, to a method and apparatus for improving the acoustic performance of an ultrasound transducer by reducing artifacts within the acoustic spectrum.

Ultrasound transducers (i.e., ultrasound probes) have found application in medical imaging where an acoustic probe is held against a patient and the probe transmits and receives ultrasound waves. The received energy may, in turn, facilitate the imaging of the internal tissues of the patient. For example, transducers may be employed to image the heart of the patient. Increasingly, it has been desirable to minimize the size of ultrasound transducers to enable their use in intra-corporeal devices, such as trans-esophageal examination devices, laparoscopic examination devices, intra-cardiac examination devices, and the like. Such applications are quite demanding, requiring very small transducer packages that can nevertheless collect large amounts of information.

Ultrasound transducers typically have many acoustical stacks arranged in one dimension or in two-dimensional (2D) arrays. Each acoustical stack corresponds to an element within the transducer, and a transducer may have many acoustical stacks therein, such as several thousand arranged in the 2D array. To minimize space and electrical capacitance in an ultrasound transducer having a 2D acoustic array, it is preferred to join the acoustic elements directly to the electronics needed for transmit and receive beam-forming. A straightforward method for attaching 2D acoustic array elements to accompanying beam-forming electronics is to directly attach these two components using a conventional method such as solder balls, gold stud bumps, plated posts, etc. With this method of connection, however, acoustic energy from the array propagates into the electronics, leading to artifacts within the acoustic spectrum ultimately reducing the image quality of a medical diagnostic image. That is, as electronic components are typically made using silicon wafers, they possess a relatively low acoustic attenuation. Therefore, when an acoustic array (such as a 2D array) is directly attached to the silicon substrate, some of the acoustic energy generated on transmit will propagate into the silicon substrate. This acoustic energy will reverberate with minimal loss within the silicon substrate and can return to the acoustic array causing long ring-down and other acoustic artifacts. These artifacts reduce the quality of the acoustic image such as those useful in medical diagnostic imaging.

The acoustic artifacts can be reduced by placing a high acoustic impedance layer (i.e., a "dematching layer") between the acoustic array and the silicon electronics. The use of such a dematching layer behind the acoustic array is well known to significantly reduce these artifacts by transforming the impedance of the layer on the reverse side of the dematching layer (i.e., the beam-forming electronics) and therefore increasing the impedance difference. However, the high impedance dematching layer itself does not reduce these artifacts sufficiently to provide the preferred image quality. That is, the ability of the dematching layer to reduce acoustic artifacts is less dramatic when the dematching layer is attached to silicon (such as the silicon substrate of the beam-forming electronics), as silicon itself possesses a fairly high acoustic impedance and low acoustic loss. An improved acoustic structure is thus required in order to provide for optimal acoustic imaging.

Therefore, it would be desirable to design an ultrasound transducer having an improved acoustic performance that reduces acoustic artifacts. It would further be desirable to maintain a minimal size for such an ultrasound transducer to enable its use as an intra-corporeal ultrasound probe.

BRIEF DESCRIPTION OF THE INVENTION

The invention is a directed method and apparatus for improving the acoustic performance of an ultrasound transducer by reducing artifacts within the acoustic spectrum. The apparatus includes an interposer layer for coupling an array of transducer elements to a beam forming electronics package.

In accordance with an aspect of the invention, an ultrasound transducer includes an acoustic layer having an array of acoustic elements, a dematching layer coupled to the acoustic layer and having an acoustic impedance greater than an acoustic impedance of the acoustic layer, and an interposer layer coupled to the dematching layer and comprising a substrate and a plurality of conductive elements, with the interposer layer having an acoustic impedance lower than the acoustic impedance of the dematching layer. The ultrasound transducer also includes an integrated circuit coupled to the interposer layer and electrically connected to the array of acoustic elements through the dematching layer and the interposer layer.

In accordance with another aspect of the invention, a method for manufacturing an ultrasound transducer includes the steps of providing an interposer layer, forming a plurality of vias in the interposer layer, adding an electrically conductive material within the vias, and coupling an acoustic layer to a dematching layer, the dematching layer having an acoustic impedance greater than an acoustic impedance of the acoustic layer and greater than an acoustic impedance of the interposer layer. The method also includes the steps of coupling the interposer layer to the dematching layer and coupling a beam forming electronics package to the interposer layer, the beam forming electronics package having a plurality of connection pads formed thereon and being electrically coupled to the acoustic layer by way of the interposer layer.

In accordance with yet another aspect of the invention, an ultrasound transducer configured for use in an invasive probe includes an acoustic layer having an array of acoustic elements, a dematching layer coupled to the acoustic layer and having an acoustic impedance greater than an acoustic impedance of the acoustic layer, and beam forming electronics configured to send signals to the acoustic layer and receive signals from the acoustic layer and having a plurality of connection pads formed thereon. The ultrasound transducer also includes an interposer layer coupled to the dematching layer, the interposer layer further including an electrically non-conductive substrate having an acoustic impedance lower than the acoustic impedance of the dematching layer and having a plurality of vias formed therein, a first connection region configured to electrically connect the beam forming electronics to the acoustic layer and having a plurality of electrically conductive pathways extending through the plurality of vias, and a second connection region configured to electrically connect the beam forming electronics to system connections including at least one of a signal input/output connection, a power and control connection, and a ground and duplicate power connection.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

Figure 1:
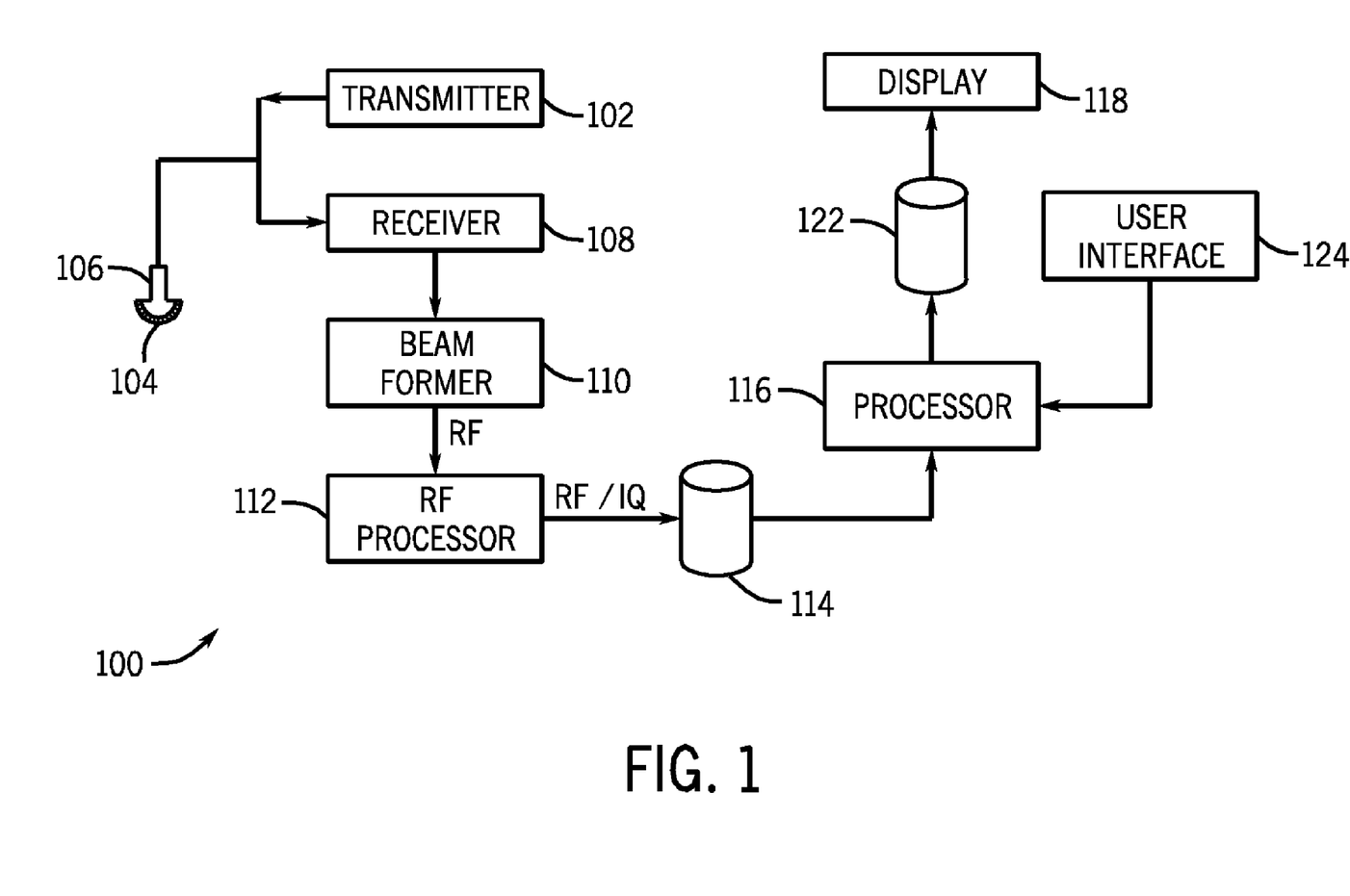
FIG. 1 illustrates a block diagram of an ultrasound system.
Figure 3:
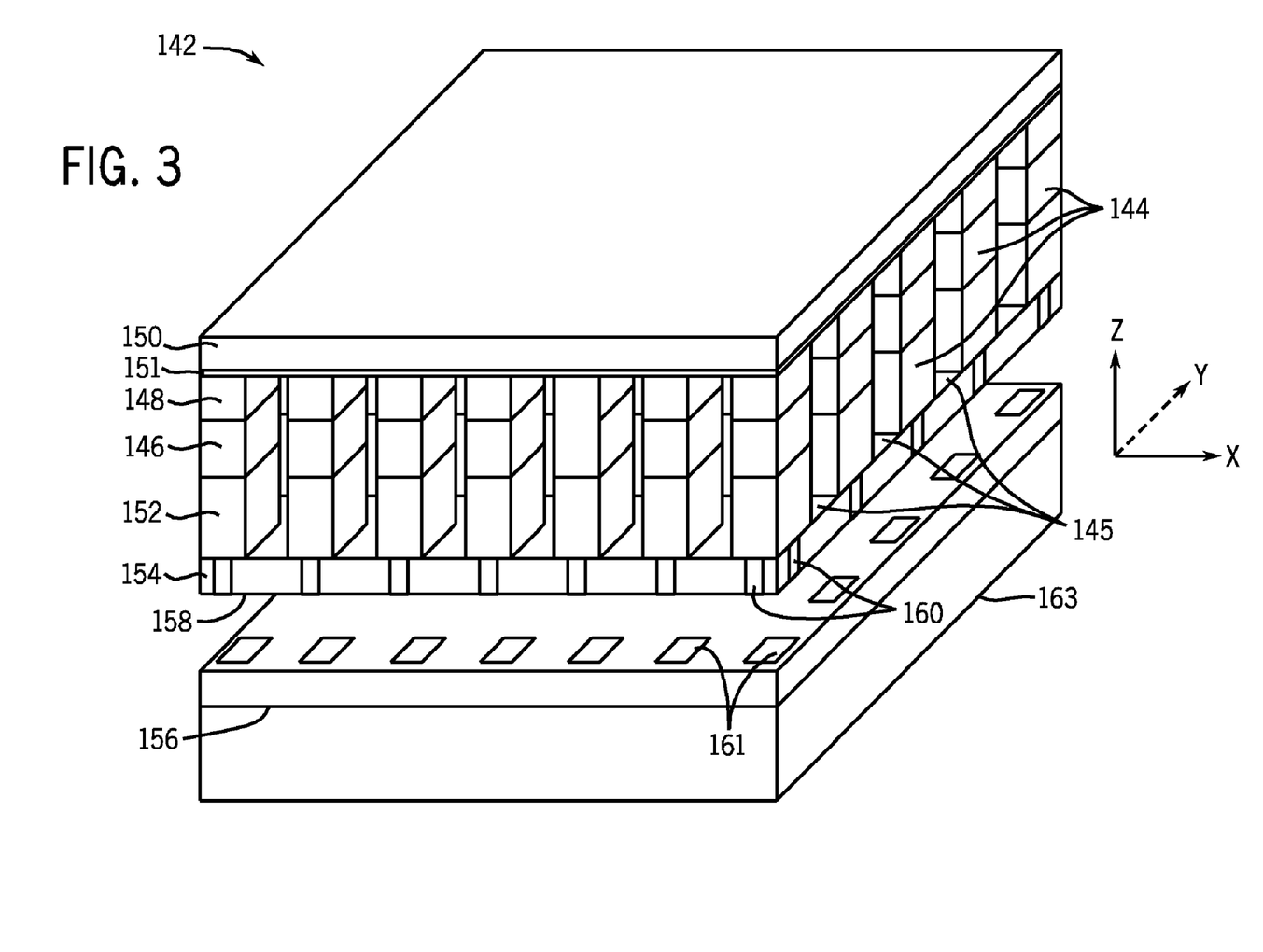
FIG. 3 is a perspective view of an exemplary embodiment of a transducer assembly for use in the ultrasound system of FIG. 1, in accordance with an embodiment of the present invention.

FIG. 1 illustrates an ultrasound system 100 including a transmitter 102 that drives an array of elements 104 (i.e., transducer elements) within an ultrasound transducer 106 to emit pulsed ultrasonic signals into a body. Each of the elements 104 corresponds to an acoustical stack (as shown in FIG. 3). The elements 104 may be arranged, for example, in one or two dimensions. A variety of geometries may be used. Each ultrasound transducer 106 has a defined center operating frequency and bandwidth. The ultrasonic signals are back-scattered from structures in the body, like fatty tissue or muscular tissue, to produce echoes that return to the elements 104. The echoes are received by a receiver 108. The received echoes are passed through beam-forming electronics 110, which performs beam-forming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and then processed and displayed in an off-line operation.

The processor module 116 is connected to a user interface 124 that may control operation of the processor module 116 as explained below in more detail. The display 118 includes one or more monitors that present patient information, including diagnostic ultrasound images to the user for diagnosis and analysis. One or both of memory 114 and memory 122 may store three-dimensional (3D) data sets of the ultrasound data, where such 3D datasets are accessed to present 2D and 3D images. Multiple consecutive 3D datasets may also be acquired and stored over time, such as to provide real-time 3D or 4D display. The images may be modified and the display settings of the display 118 also manually adjusted using the user interface 124.

Figure 2:
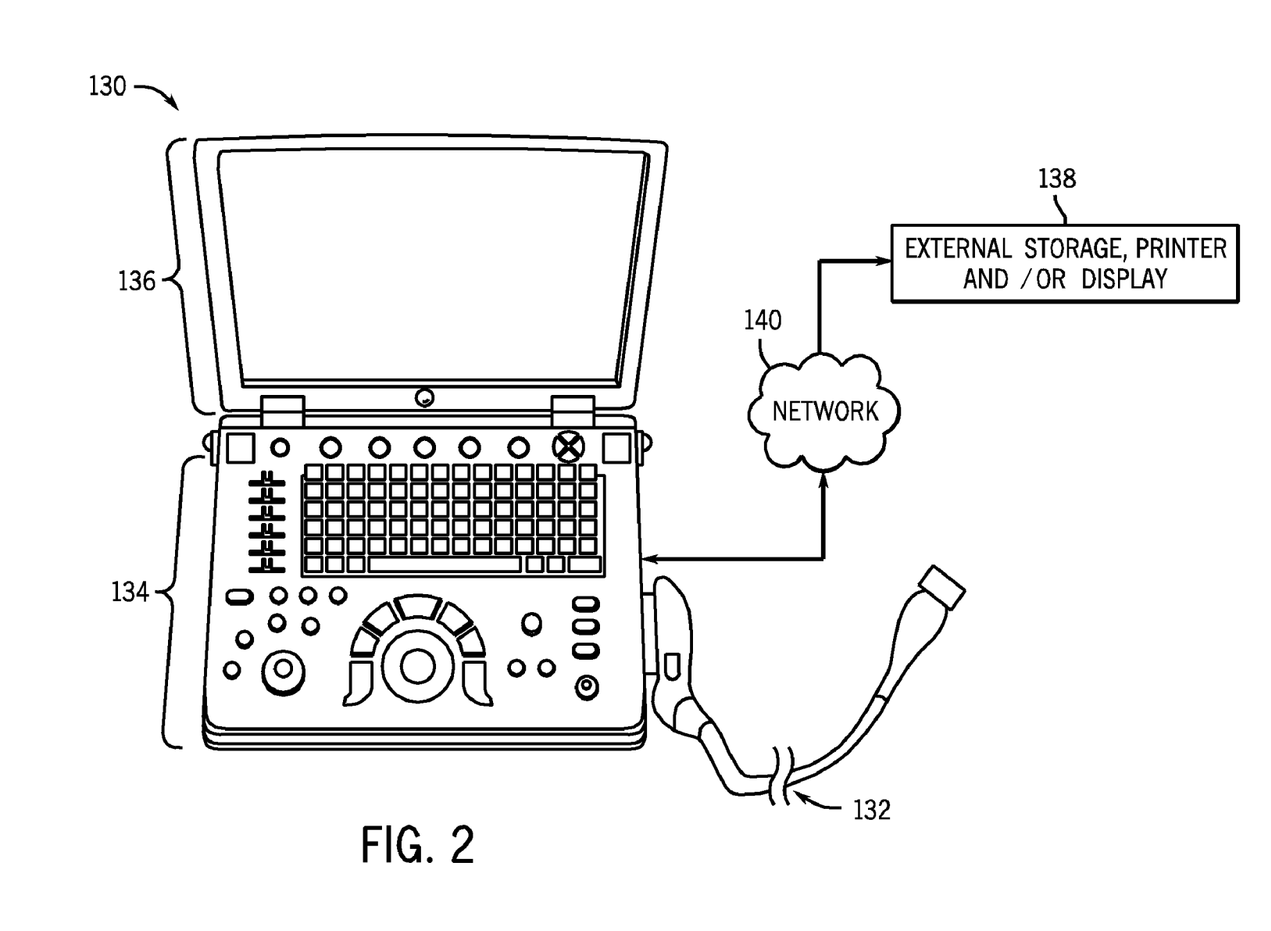
FIG. 2 illustrates a miniaturized ultrasound system having a transducer that may be configured to acquire ultrasonic data in accordance with an embodiment of the present invention.

FIG. 2 illustrates a 3D-capable miniaturized ultrasound system 130 having a transducer 132 that may be configured to acquire 3D ultrasonic data. For example, the transducer 132 may have a 2D array of transducer elements 104 as discussed previously with respect to the ultrasound transducer 106 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136.

As another example, the ultrasound system 130 may be a 3D capable pocket-sized ultrasound system. By way of example, the pocket-sized ultrasound system may be approximately 2 inches wide, approximately 4 inches in length, and approximately 0.5 inches in depth and weigh less than 3 ounces. The pocket-sized ultrasound system may include a display, a user interface (i.e., keyboard) and an input/output (I/O) port for connection to the transducer (all not shown). It should be noted that the various embodiments may be implemented in connection with a miniaturized ultrasound system having different dimensions, weights, and power consumption.

Referring now to FIG. 3, a perspective view of an exemplary embodiment of a transducer assembly 142 incorporated into ultrasound transducer 106 (FIG. 1) and/or transducer 132 (FIG. 2) is illustrated according to an embodiment of the invention. The transducer assembly 142 is shown as including an array of transducer elements 144, formed as acoustic stacks including a plurality of layers, that are formed in a spaced apart relationship according to a desired inter-element space or pitch 145. Included in each transducer element 144 is an acoustic layer 146 or acoustic element, such that an array of acoustic elements is provided in transducer assembly 142. The acoustic layer 146 has a first surface and a second surface, where the second surface is opposite the first surface. In one embodiment, the first surface may include a top surface and the second surface may include a bottom surface.

As will be appreciated, the acoustic layer 146 may be configured to generate and transmit acoustic energy into a patient (not shown) and receive backscattered acoustic signals from the patient to create and display an image. The acoustic layer 146 may include electrodes (not shown) on the top and bottom surfaces, as known in the art. The acoustic layer 146 may be formed of a piezoelectric ceramic such as lead zirconate titanate (PZT), a piezocomposite, a piezoelectric single crystal, or a piezopolymer. It may be noted that in certain embodiments, the acoustic layer 146 may include multiple layers of the aforementioned materials. More particularly, in one embodiment, the acoustic layer 146 may include multiple layers of the same material, while in another embodiment, the acoustic layer 146 may include multiple layers of different materials.

As shown in FIG. 3, each transducer element 144 may include at least one matching layer disposed on the first surface of the acoustic layer 146. It may be noted that the at least one matching layer may be configured to have an acoustic impedance less than the acoustic impedance of the acoustic layer 146. For example, the acoustic impedance of the at least one matching layer may be in a range from about 2 MRayls to about 15 MRayls, while the acoustic impedance of the acoustic layer 146 may be in a range from about 3 MRayls to about 35 MRayls.

In one embodiment, a first matching layer 148, itself having a top surface and a bottom surface, may be disposed on the first surface of the acoustic layer 146. As will be appreciated, the first matching layer 148 may be configured to facilitate the matching of an impedance differential that may exist between the high impedance transducer elements and, for example, a low impedance patient. In a presently contemplated configuration, the first matching layer 148 may include filled epoxy, metal-impregnated graphite, or glass ceramics.

In a presently contemplated configuration, each transducer element 144 may also include a second matching layer 150 having a top surface and a bottom surface disposed on the top surface of the first matching layer 148. As noted with respect to the first matching layer 148, the second matching layer 150 may also be configured to facilitate the matching of an impedance differential that may exist between the high impedance transducer elements and a low impedance patient. Also, as previously noted with reference to the first matching layer 148, in a presently contemplated configuration, the second matching layer 150 may include unfilled epoxy or plastic, such as polysulphone or polystyrene. While first and second matching layers 148, 150 are shown as included in transducer elements 144, it is recognized that a lesser or greater number of matching layers could be employed. As such, a single matching layer could be used, or third and fourth matching layers could be added to the first and second matching layers.

According to one embodiment, first matching layer 148 is composed of an electrically conductive material. The second matching layer 150 is applied onto first matching layer 148 as a continuous layer and includes a conductive film 151 on the bottom surface thereof. The continuous second matching layer 150 (and conductive film 151) thus provides an electrical ground connection for each of the transducer elements 144. It is recognized that, according to another embodiment, the first matching layer could be electrically non-conductive and have a conductive layer forming on the bottom surface thereof, and thus be formed as a continuous layer. It is further recognized that, according to an exemplary embodiment, a facing (not shown) such as silicone or polyurethane can be placed on the top surface of second matching layer 150, to configure transducer assembly 142 for use with a patient.

As further shown in FIG. 3, each transducer element 144 may include a dematching layer 152 disposed adjacent the bottom surface of the acoustic layer 146. The dematching layer 152 is disposed on the bottom surface of the acoustic layer 146 and coupled thereto. The dematching layer 152 may be constructed employing a material having an impedance substantially higher than the acoustic impedance of the acoustic layer 146. For example, the acoustic impedance of the acoustic layer 146 may be in a range from about 3 MRayls to about 35 MRayls, while the acoustic impedance of the dematching layer 152 may be in a range from about 60 MRayls to about 100 MRayls, and preferably above 70 MRayls. In certain embodiments, the high impedance material may be formed of tungsten carbide, although it is recognized that tungsten, tantalum, or other materials with similar acoustic impedance could be used. The dematching layer 152 functions as an acoustic impedance transformer, dramatically increasing the effective acoustic impedance presented at (or experienced by) the rear face of the acoustic layer 146 to a value substantially greater than the impedance of the acoustic layer 146. Consequently, a majority of the acoustic energy is reflected out a front face of the acoustic layer 146.

Coupled to a bottom surface of the dematching layer 152 (and to a bottom surface of acoustic stacks 144) is an interposer layer 154 configured to operatively couple the acoustic layer of each transducer element 144 to an integrated circuit 156 configured to perform beam-forming (i.e., "beam-forming electronics") included in the transducer assembly 142 of ultrasound transducer 106 (FIG. 1). The interposer layer 154 is formed of a low acoustic impedance material. The combination of interposer layer 154 and integrated circuit 156 acts as an acoustic load on the back face of dematching layer 152. The dematching layer 152 operates as an acoustic impedance transformer, thereby presenting the transformed impedance of the acoustic load to the back face of the acoustic layer element 146. Without the interposer, the acoustic impedance presented to the back of the acoustic layer is less then it is when the interposer is present. So by including the low acoustic impedance interposer 154, the acoustic element reflects more acoustic energy out the front face of the acoustic layer 146, thereby reducing acoustic artifacts in the transducer assembly 142. Placement of interposer layer 154, which is formed of a low acoustic impedance material, between dematching layer 152 and beam-forming electronics 156 dramatically increases the effective acoustic impedance of the beam-forming electronics 156, thereby reflecting a majority of the acoustic energy out the front/top face of the acoustic layer 146 and reducing the presence of acoustic artifacts in transducer assembly 142.

According to an exemplary embodiment, interposer layer 154 is formed of an electrically non-conductive organic substrate 158 having an acoustic impedance of less than approximately 10 MRayls, and preferably less than 5 MRayls. The organic substrate 158 may be composed of a polyimide such as Kapton® polyimide, for example. Also included in interposer layer 154 is a plurality of electrically conductive elements 160 that extend through the substrate 158, so as to provide an electrical connection or pathway between beam-forming electronics 156 and dematching layer 152 (and subsequently to acoustic layer 146). As shown in FIG. 3, a spacing or pitch of the conductive elements 160 is such that an electrical connection is formed between interconnect pads 161 on beam-forming electronics 156 and each transducer element 144.

It is recognized that a thin interposer layer 154 may not provide enough loss to eliminate the trapping of ultrasound waves in dematching layer 152 and/or beam-forming electronics 156 that might later leak back into acoustic layer 146. Thus, according to an embodiment of the invention, a lossy backing layer 163 is added to a back surface of beam-forming electronics 156. In a preferred embodiment, lossy backing layer 163 is formed, for example, of scatters such as heavy metal powders mixed in a lossy polymer, such as epoxy or PVC. When formed of these (or similar) materials, backing layer 163 has an acoustic impedance less than or equal to the acoustic impedance of the beam-forming electronics 156. The high attenuation/scattering properties of lossy backing layer 163 helps prevent ultrasound waves from becoming trapped in dematching layer 152 and/or beam-forming electronics 156 that might later leak back into acoustic layer 146. Lossy backing layer 163 thus functions to further reduce artifacts within the acoustic spectrum.

It may be noted that a thicknesses of each of the acoustic layer 146, the first matching layer 148, the second matching layer 150, the dematching layer 152, and the interposer layer 154 may be determined/selected according to the application that entails the use of the transducer assembly 142. More particularly, different applications of the transducer assembly 142 may call for a diverse range of frequencies of operation. The thickness of each of the constituent layers 146, 148, 150, 152, 154 of the transducer assembly 142 may accordingly be determined based upon the application that involves use of the transducer assembly 142. According to one embodiment, the thickness of layers 146, 148, 150, 152, 154 are scaled based on the transducer assembly 142 operating at a "specific frequency," usually the center frequency. According to another embodiment, the thickness of layers 146, 148, 150, 152, 154 are scaled differently based on the use of the transducer assembly 142 at several different frequencies. That is, for harmonics where acoustic layer 146 transmits at one frequency and receives at a different frequency, the thicknesses of the dematching layer 152 and matching layers 148, 150 are selected to optimize these transmit and receive functions.

Figure 4:
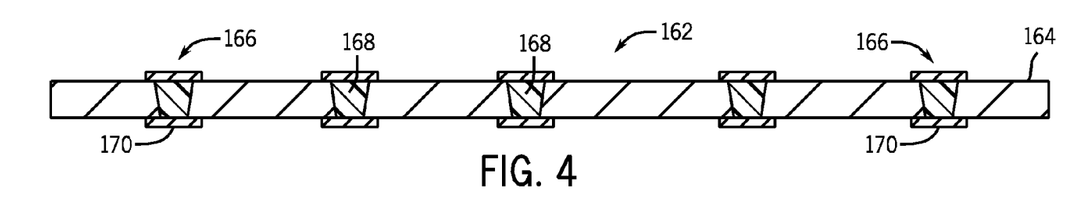
FIG. 4 is a cross-sectional view of an interposer layer of the transducer assembly perspective in accordance with an embodiment of the present invention.
Figure 5:
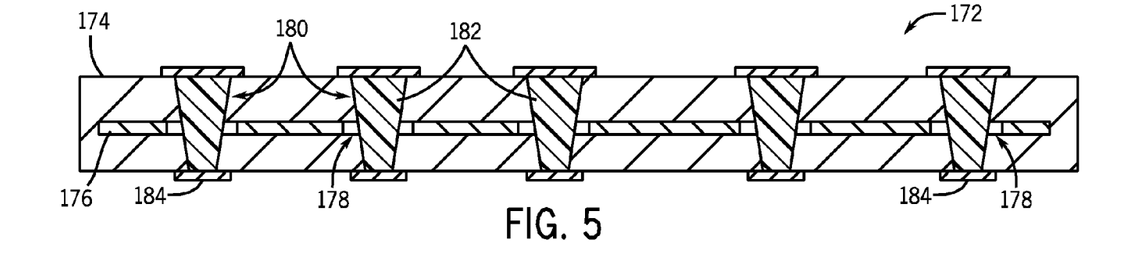
FIG. 5 is a cross-sectional view of an interposer layer of the transducer assembly perspective in accordance with another embodiment of the present invention.
Figure 6:
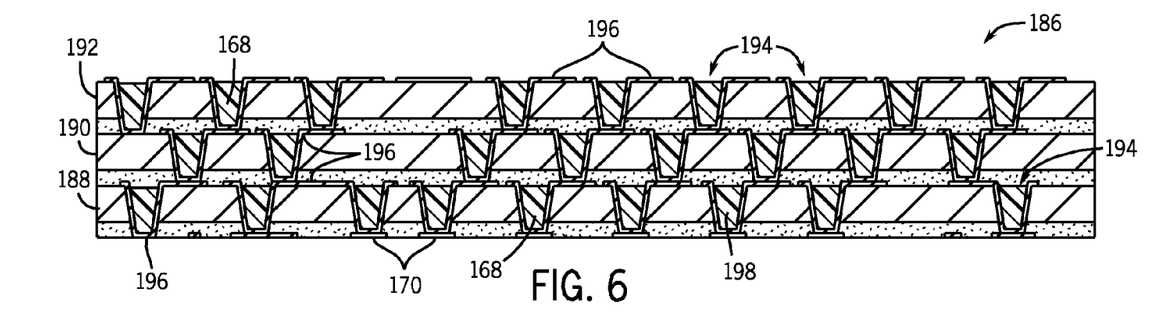
FIG. 6 is a cross-sectional view of an interposer layer of the transducer assembly perspective in accordance with another embodiment of the present invention.

Referring now to FIGS. 4-6, a more detailed view of interposer layer 154 is shown according to embodiments of the invention. It is recognized that conductive elements 160 in interposer layer 154 may take several forms to provide an electrical connection or pathway between beam-forming electronics 156 and dematching layer 152 (and subsequently to acoustic layer 146). According to one embodiment of the invention, conductive element 160 is in the form of an electrically conductive filler material having a low acoustic impedance, such as silver epoxy. According to another embodiment of the invention, it is recognized that the conductive element could be in the form of a conductive interconnect, such as a thin layer of plated copper having a thickness of 1-10 microns, that is used in combination with a low impedance non-conductive epoxy.

Referring to FIG. 4, an interposer layer 162 is shown for use with the transducer assembly 142 of FIG. 3, according to an embodiment of the invention. Interposer layer 162 is shown as being formed of a single-layer, electrically non-conductive organic substrate 164. The substrate 164 may be formed of Kapton® polyimide, for example, and have an acoustic impedance of less than approximately 10 MRayls, and preferably less than 5 MRayls. The substrate 164 includes a plurality of vias 166 formed therein that are configured as thru-vias extending from a front surface to a back surface of the substrate. According to the embodiment of FIG. 4, vias 166 are formed in substrate 164 to have a spacing or pitch identical to that of the transducer elements 144 (and acoustic elements 146) of the transducer assembly 142, as shown in FIG. 3.

Each of the vias 166 is filled with an electrically conductive filler material 168 that provides an electrical connection or pathway through interposer layer 162. According to an exemplary embodiment of the invention, the filler material 168 has an acoustic impedance similar to the acoustic impedance of the substrate 164. For example, the filler material 168 contained within vias 166 may be a silver epoxy having an acoustic impedance of approximately 3 MRayls. A plurality of connection pads 170 are located on top and bottom surfaces of the interposer layer 162 at locations corresponding to each of the vias 166. Filler material 168 and connection pads 170 thus provide an electrical connection/pathway between interconnect pads 161 of beam-forming electronics 156 and each of the transducer elements 144 of the transducer assembly 142, as shown in FIG. 3.

Referring now to FIG. 5, a more detailed view of an interposer layer 172 is shown for use with the transducer assembly 142 of FIG. 3, according to another embodiment of the invention. Interposer layer 172 is shown as being formed of a single-layer, electrically non-conductive organic substrate 174. The substrate 174 may be formed of polyimide, for example, and have an acoustic impedance of less than approximately 10 MRayls, and preferably less than 5 MRayls. Embedded within substrate 174 is a metallic sheet 176 having a plurality of perforations 178 formed therein. A plurality of vias 180 are formed in substrate 174 and are configured as thru-vias extending from a front surface to a back surface of the substrate and through perforations 178 in metallic sheet 176. According to the embodiment of FIG. 5, vias 180 are formed in substrate 174 to have a spacing or pitch identical to that of the transducer elements 144 (and acoustic elements 146) of the transducer assembly 142, as shown in FIG. 3. As such vias 180 may be formed through each of the perforations 178 in metallic sheet 176 or only a portion of the perforations, depending on a pitch of the perforations in the metal sheet. Beneficially, metal sheet 176 lowers the amount of thermal expansion in the x and y directions undergone by interposer layer 172 as compared to an interposer layer formed solely from an organic material substrate. According to an exemplary embodiment, metal sheet makes up less than 25% of the total interposer layer structure.

As further shown in FIG. 5, each of the vias 180 is filled with an electrically conductive filler material 182 that provides an electrical connection or pathway through interposer layer 172. According to an exemplary embodiment of the invention, the filler material 182 has an acoustic impedance similar to the acoustic impedance of the substrate 174. For example, the filler material 182 contained within vias 180 may be a silver epoxy having an acoustic impedance of approximately 3 MRayls. A plurality of connection pads 184 are located on top and bottom surfaces of the interposer layer 172 at locations corresponding to each of the vias 180. Filler material 182 and connection pads 184 thus provide an electrical connection/pathway between interconnect pads 161 of beam-forming electronics 156 and each of the transducer elements 144 of the transducer assembly 142, as shown in FIG. 3.

Referring now to FIG. 6, a more detailed view of an interposer layer 186 is shown for use with the transducer assembly 142 of FIG. 3, according to another embodiment of the invention. Interposer layer 186 is shown as being formed as a multi-layer structure having a plurality of distinct substrate layers 188, 190, 192. While interposer layer 186 is shown as including three substrate layers, a bottom layer 188, a middle layer 190, and a top layer 192, it is envisioned that a greater or lesser number of layers could be implemented. Each of substrate layers 188, 190, 192 is formed of an electrically non-conductive organic substrate having a low acoustic impedance (e.g., <10 MRayls, and preferably <5 MRayls), such as polyimide. Each of substrate layers 188, 190, 192 includes a plurality of vias 194 formed therein extending from a front surface of a layer to a back surface of that layer. According to the embodiment of FIG. 6, a pitch of vias 194 formed in each of substrate layers 188, 190, 192 differ from one another, to allow for connection of interposer layer 186 to transducer elements 144 (and acoustic elements 146) (FIG. 3) having a first pitch and interconnect pads 161 of beam-forming electronics 156 (FIG. 3) having a second pitch different from the first pitch.

As shown in FIG. 6, vias 194 formed in bottom substrate layer 188 have a first pitch that matches a pitch of interconnect pads 161 of beam-forming electronics 156. According to an exemplary embodiment of the invention, each of the vias 166 in bottom substrate layer 188 has a metal interconnect 196 formed therein. The metal interconnects 196 are formed of a thin layer (e.g., 1-10 microns thickness) of conductive material, such as copper, and each interconnect is stamped to substantially conform to the via and extend onto a top surface of substrate layer 188. Each of vias 194 in bottom substrate layer 188 is also filled with an low impedance electrically non-conductive filler material 198, that is deposited on the metal interconnect that extends down into via, so as to form a via structure having a substantially similar acoustic impedance (e.g., approximately 3 MRayls) as the substrate layer. A plurality of connection pads 170 are located on the bottom surface of bottom substrate layer 188 at locations corresponding to each of the vias 194.

Vias 194 are also formed in middle substrate layer 190, with the vias in the middle substrate layer having a second pitch different from the pitch of the vias in bottom substrate layer 188. Vias 194 in middle substrate layer 190 are formed at locations that overlap/intersect with the metal interconnects 196 of the bottom layer vias, such that an electrical connection can be formed between the bottom and middle substrate layers 188, 190. Similar to bottom substrate layer 188, each of vias 194 in middle substrate layer 190 also have a metal interconnect 196 formed therein, that extends down through the via and also onto a top surface of substrate layer 190. Each of vias 194 in middle substrate layer 190 is filled with an electrically non-conductive filler material 198, that is deposited on the metal interconnect that extends down into via, so as to form a via structure having a substantially similar acoustic impedance as the substrate layer.

Vias 194 are also formed in top substrate layer 192, with the vias in the top substrate layer having a third pitch different from the pitch of the vias in bottom and middle substrate layer 188, 190. Vias 194 in top substrate layer 192 are formed at locations that overlap/intersect with the metal interconnects 196 of the middle layer vias, such that an electrical connection can be formed between the middle and top substrate layers 190, 192. The pitch of vias 194 in top substrate layer 192 also matches a pitch of to transducer elements 144 (and acoustic elements 146). Each of vias 194 in top substrate layer 192 also have a metal interconnect 196 formed therein, that extends down through the via and also onto a top surface of top substrate layer 192, and can extend onto an outward facing surface of the top substrate layer to form a connection pad. Each of vias 194 in top substrate layer 192 is filled with an electrically non-conductive filler material 198 that is deposited on the metal interconnect that extends down into via, so as to form a via structure having a substantially similar acoustic impedance as the substrate layer. A plurality of connection pads 170 are located on the top surface of top substrate layer 192 at locations corresponding to each of the vias 194.

The multi-layer substrate of interposer layer 186 provides for a rerouting of connection pads 170 on outward facing surfaces thereof, such that connection pads on bottom substrate layer 188 have a pitch different from connection pads on top substrate layer 192. Interposer layer 186 thus allows for connection of transducer elements 144 having a first pitch to beam-forming electronics 156 having interconnect pads 161 with a second pitch different from the first pitch.

In each of the embodiments of FIGS. 4-6, it is recognized that the conductive elements/pathways formed in the interposer layer could take the form of a conductive epoxy or of a non-conductive epoxy used in conjunction with a thin metal conductive interconnect. Thus, the specific form of the conductive element in each of the embodiments of FIGS. 4-6 could be substituted with the alternative form of the conductive element. For example, the conductive epoxy set forth in the embodiment of FIG. 4 could be replaced by a non-conductive epoxy used in conjunction with a thin metal conductive interconnect, and a similar substitution could be made for each of the embodiments of FIGS. 5 and 6.

Figure 7:
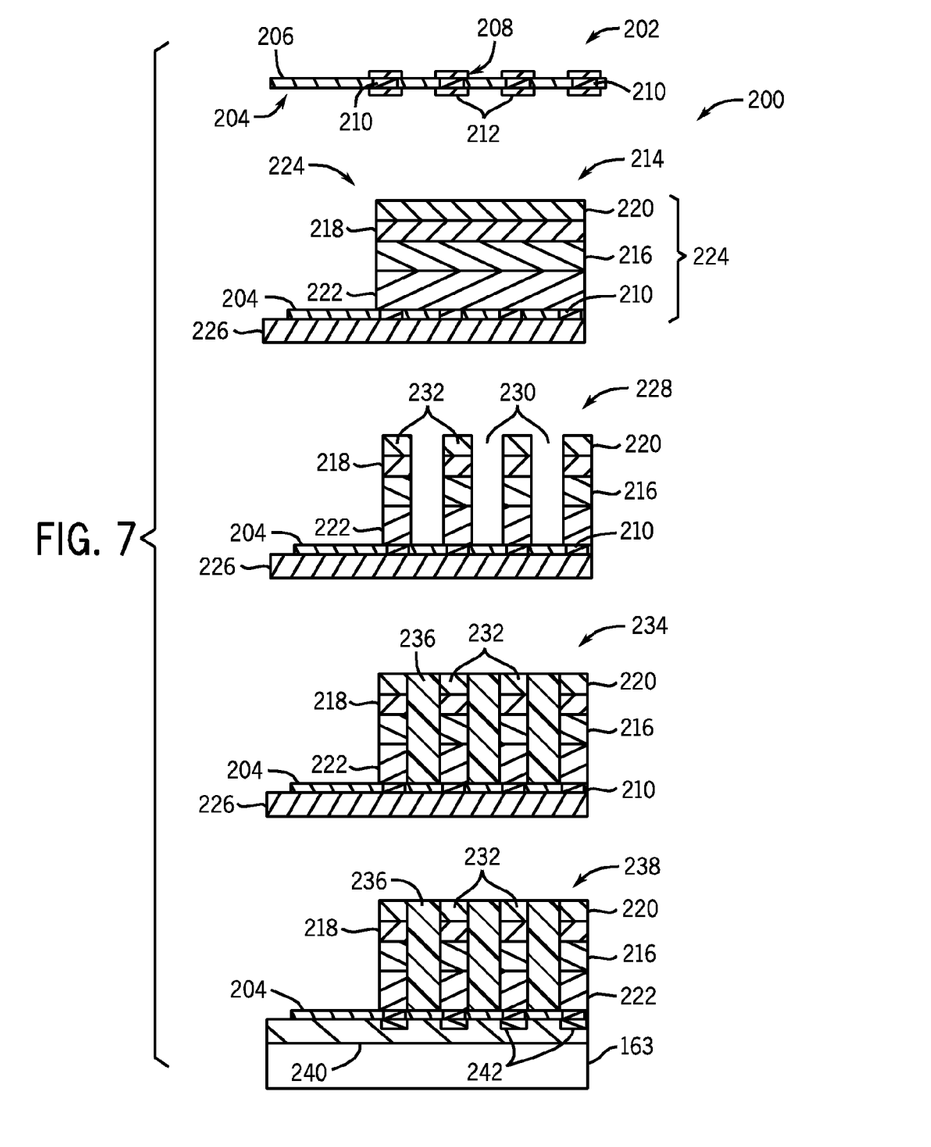
FIG. 7 is a series of schematic sectional views of progressive formation of a transducer assembly in accordance with an embodiment of the present invention.

Turning now to FIG. 7, progressive structures are illustrated, made in an exemplary process 200 of fabricating an exemplary transducer assembly, such as the transducer assembly 142 shown in FIG. 3, in accordance with an embodiment of the present invention. The process begins at step 202 where an interposer layer 204 is provided. In the embodiment of FIG. 7, interposer layer 204 is shown as being formed of a single-layer substrate 204, but it is recognized that a multi-layer substrate could also be provided according to the embodiment of FIG. 6. The interposer layer substrate 206 is an electrically non-conductive organic substrate that may be formed of polyimide, for example, and have an acoustic impedance of less than approximately 10 MRayls, and preferably less than 5 MRayls. A plurality of vias 208 is formed in the substrate, which are configured as thru-vias extending from a front surface to a back surface of the substrate 206. According to the embodiment of FIG. 7, vias 208 are formed in substrate 206 to have a spacing or pitch identical to that of the transducer elements 144 (and acoustic elements 146) of the transducer assembly 142 (FIG. 3), as will be explained below. Each of the vias 208 is filled with an electrically conductive filler material 210 that provides an electrical connection or pathway through interposer layer 204. According to an exemplary embodiment of the invention, the filler material 210 has an acoustic impedance similar to the acoustic impedance of the substrate 206. For example, the filler material 210 contained within vias 208 may be a silver epoxy having an acoustic impedance of approximately 3 MRayls. A plurality of connection pads 212 are then added on top and bottom surfaces of the interposer layer 206 at locations corresponding to each of the vias 208.

Following formation of the interposer layer 204, an exemplary transducer assembly is formed at step 214, such as the transducer assembly 142 (see FIG. 3). An acoustic layer 216 having a top surface and a bottom side is provided. Electrodes (not shown) may be sputtered and/or plated on the top and bottom sides of the acoustic layer 216. As will be appreciated, the electrodes may have different physical configurations, particularly for ground and signal electrodes. In one embodiment, the electrodes may include a wrap-around configuration. The acoustic layer 216 may be configured to have a thickness in a range from about 50 microns to about 600 microns.

A first matching layer 218 having a top surface and a bottom surface may be disposed on the top surface of the acoustic layer 216. The first matching layer 218 may be configured to have a thickness in a range from about 40 microns to about 300 microns. Subsequently, a second matching layer 220 having a top surface and a bottom surface may be disposed on the top surface of the first matching layer 218. As described with respect to the first matching layer 218, the second matching layer 220 may be configured to have a thickness in a range from about 30 microns to about 250 microns. The first and second matching layers 218, 220 may be configured to facilitate the matching of an impedance differential that may exist between the high impedance acoustic layer 216 and a low impedance patient. It may be appreciated that such transducers may include a single or multiple matching layers. Currently available transducers typically employ two matching layers, where the use of two matching layers in the transducers may represent the best trade-off between performance and stack thickness for space-constrained applications.

Additionally, at step 214, an exemplary dematching layer 222 having a top surface and a bottom surface may be disposed on the bottom surface of the acoustic layer 216. In other words, the dematching layer 222 may be disposed on a surface of the acoustic layer 216 that is opposite the surface that the first matching layer 218 is disposed on. Furthermore, the dematching layer 222 may be configured to have a thickness in a range from about 50 microns to about 500 microns. Moreover, as will be appreciated, the dematching layer 222 may be configured to be electrically conductive, either by being formed of an electrically conductive substrate or by being formed of an electrically non-conductive substrate with conductive via structures formed therein. A pre-diced acoustic stack 224 may thus be formed by stacking the second matching layer 220, the first matching layer 218, the acoustic layer 216 and the dematching layer 222, and bonding the layers together.

With continuing reference to step 162, interposer layer 204 is coupled to the bottom surface of the dematching layer 222. Such coupling can be performed by way of any of several known methods, including: compressive bonding, gold stud bump bonding, conductive epoxy, solder reflow, anisotropically conductive films, or other methods. As set forth above, interposer layer 204 has an acoustic impedance substantially less than the acoustic impedance of dematching layer 222. As further shown in FIG. 7, a substrate 226 having a top surface and a bottom surface may be selected. The substrate 226 may include one of a plastic, a metal, a ceramic, silicon, a polymer or glass. It may be noted that the substrate 226 may be configured to provide mechanical strength to the transducer assembly during the fabrication process.

Step 228 depicts dicing of the transducer assembly to form a plurality of transducer elements. Accordingly, one or more saw kerfs 230 may extend through the second matching layer 220, the first matching layer 218, the acoustic layer 216 and the dematching layer 222. In accordance with further aspects of the present technique, the one or more saw kerfs 230 may also partially extend into the interposer layer 204. Consequent to the dicing of the four layers at step 228, a plurality of transducer elements 232 may be formed.

At step 234, a kerf filler material 236 may be disposed in the inter-element spaces between the plurality of transducer elements 232. Alternatively, the kerfs 230 may be left unfilled such that air is present between each of transducer elements 232. The kerf filler 236 may include filled or unfilled silicone or epoxy. Also, the kerf filler 236 may be configured to mechanically strengthen the transducer assembly by filling the inter-element space 230 thereby resulting in a less fragile and more reliable assembly. The kerf filler 236 may be configured to have low shear stiffness or high shear attenuation, thereby resulting in minimized inter-element cross talk. Following step 234, the substrate 226 may be removed, at step 238, and beam-forming electronics 240 coupled to a bottom surface of interposer layer 204, such as by compressive bonding, gold stud bump bonding, conductive epoxy, solder reflow, anisotropically conductive films, or other methods. A lossy backing layer 241 may also be added to a back surface of beam-forming electronics 240. As shown in FIG. 7, a spacing or pitch of interconnect pads 242 on beam-forming electronics 240 matches a pitch of connection pads 212 on interposer layer 204 such that an electrical connection is formed between beam-forming electronics 240 and interposer layer 204.

It is recognized that alternate fabrication processes could be implemented for constructing a transducer assembly 142 other than the fabrication process set forth in FIG. 7. For example, according to alternate fabrication process embodiments, the substrate 226 could be removed from the fabrication process. According to one embodiment, a fabrication process could begin by attaching interposer layer 204 to beam-forming electronics 240. The acoustic stack 224 could then be built-up on interposer layer 204 and beam-forming electronics 240 (which provides support), thereby negating the need for substrate 226. According to another embodiment, acoustic stack 224 could be built-up on only interposer layer 204. The beam-forming electronics 240 would then be subsequently attached to interposer layer 204, such that the beam-forming electronics are not subjected to the forming process of transducer elements 232. According to another embodiment, acoustic stack 224 could be diced before addition of second matching layer 220, such that the second matching layer remains as a continuous layer and, along with a conductive film (not shown) applied on the bottom surface thereof, provides an electrical ground connection for each of the transducer elements 232.

Figure 8:
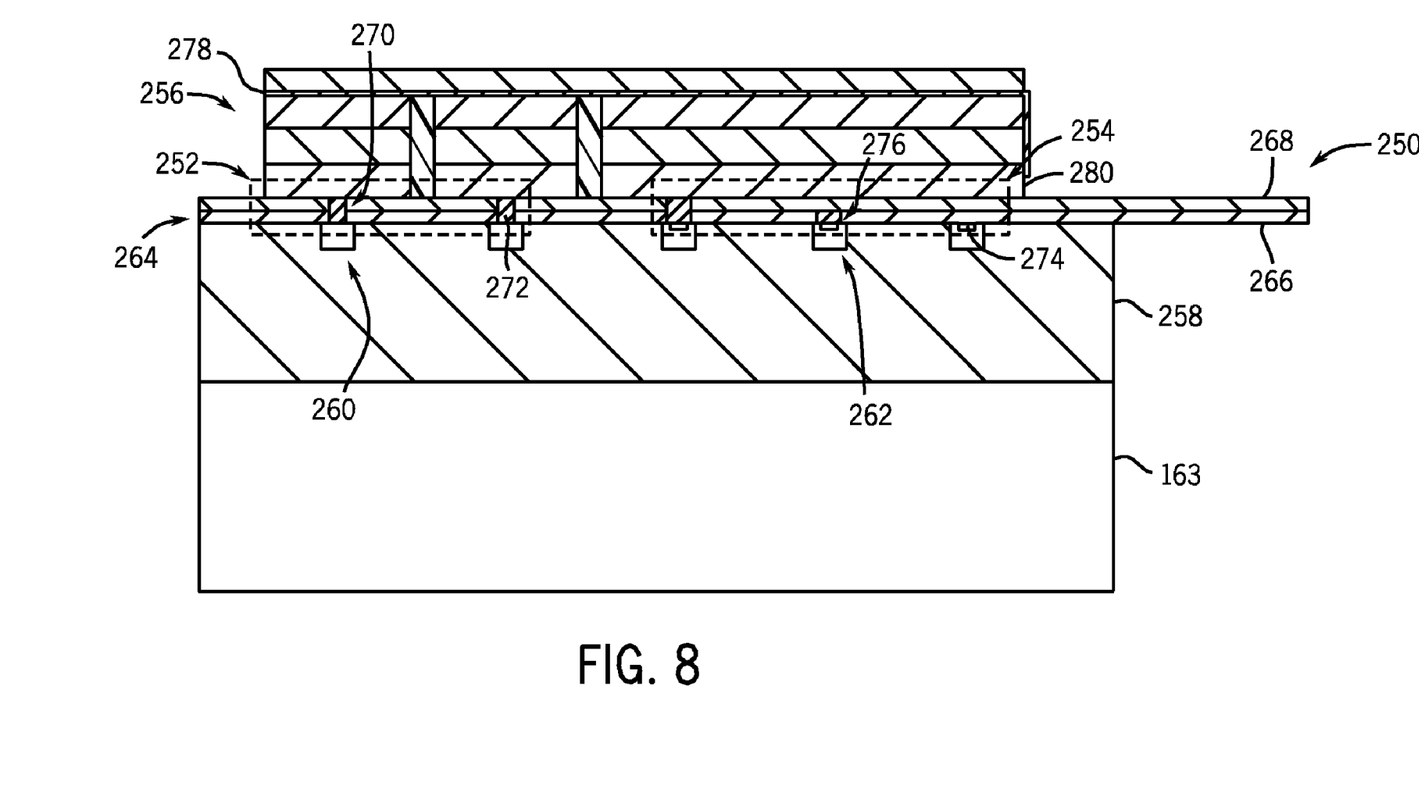
FIG. 8 is a cross-sectional view of a transducer assembly, interposer layer, and beam-forming electronics in accordance with an embodiment of the present invention.

Referring now to FIG. 8, according to an embodiment of the invention, an interposer layer 250 is provided that is configured to allow for simultaneous connection to transducer elements and to interconnects on beam forming electronics. The interposer layer 250 includes a first connection region 252 and a second connection region 254 for coupling to transducer elements 256, such as described in FIG. 3, and beam-forming electronics 258, respectively. The first connection region 252 and second connection region 254 of interposer layer 250 correspond to first and second groups of interconnect pads 260, 262 on beam-forming electronics 258. The first group of interconnect pads 260 is located within the center portion of the beam-forming electronics 258 and are associated with the transducer elements 256, whereas the second group of interconnect pads 262 is located along one or more edges of the beam-forming electronics 258 and are associated with system connections that provide signal input/output (I/O), power, and control functions.

Similar to the interposer layers discussed in FIGS. 3-7, interposer layer 250 is formed of an electrically non-conductive organic substrate 264. According to an exemplary embodiment, substrate 264 is formed of an electrically non-conductive material having an acoustic impedance of less than approximately 10 MRayls, and preferably less than 5 MRayls. The organic substrate 264 may be composed of polyimide, for example, and have a total thickness in a range from about 25 microns to about 500 microns, and preferably above 125 microns. The interposer layer 250, being formed of a low acoustic impedance material, allows for dematching layer 280, interposer layer 250, and integrated circuit 258 to function more efficiently as an acoustic reflector. Placement of the low acoustic impedance interposer layer 250 between dematching layer 280 and beam-forming electronics 258 dramatically increases the effective acoustic impedance of the beam-forming electronics, thereby reflecting a majority of the acoustic energy out the front/top face of the transducer elements 256.

As shown in FIG. 8, substrate 264 of interposer layer 250 includes a first layer 266 and a second layer 268, although it is recognized that other single or multi-layer substrates could also be implemented. According to an exemplary embodiment, in the second connection region 254, first layer 266 of substrate 264 functions as a signal I/O for carrying signals between beam-forming electronics 258 and a system connection (not shown), such as a cable flex circuit. Second layer 268 of substrate 264 functions as a power and control layer for providing power/control signals from the system connection to beam-forming electronics 258.

The first connection region 252 of interposer layer 250 includes a plurality of vias 270 formed therein that are configured as thru-vias extending from a front surface to a back surface of the substrate. As set forth above with respect to FIG. 4, vias 270 are formed in substrate 264 to have a spacing or pitch identical to that of the transducer elements 256 and to a pitch of interconnect pads in group 260 (e.g., bump connections) of beam-forming electronics 258. Each of the vias 270 is filled with an electrically conductive filler material 272 (e.g., silver epoxy) or with a thin metal conductive interconnect and electrically non-conductive epoxy, that provides an electrical connection or pathway through interposer layer 250 first group of interconnect pads 260 of beam-forming electronics 258 and each of the transducer elements 256.

The second connection region 254 of interposer layer 250 functions to transmit power and control commands from a system interconnect, such as a cable flex circuit, to beam-forming electronics 258. Second connection region 254 thus includes conductive traces (not shown) running therethrough, as well as a series of pad connections 274 and/or vias 270 (filled with conductive epoxy 272) that correspond to the second group of interconnect pads 262 on beam-forming electronics 258. According to an exemplary embodiment, a connection pad 274 on interposer layer 250 electrically couples first substrate layer 266 to an interconnect pad in the second group of interconnect pads 262 to provide a signal I/O to beam-forming electronics 258. To provide power and control signals to beam-forming electronics 258, second substrate layer 268 is electrically coupled to another interconnect pad in the second group of interconnect pads 262 by way of a single layer via 276 (filled with conductive epoxy 272) extending through first substrate layer 266 (filled with an electrically conductive material) and a connection pad 274. A ground/duplicate power connection between another interconnect pad in the second group of interconnect pads 262 and an electrical ground 278 is also provided by interposer layer 250. That is, a through via 270 filled with conductive epoxy 272 is formed through substrate 264 to electrically couple an interconnect pad in the second group of interconnect pads 262 to an electrically conductive dematching layer 280, which is further coupled to electrical ground 278.

As shown in FIG. 8, according to an exemplary embodiment, the acoustic stack forming transducer elements 256 is of sufficient size to cover both first connection region 252 and second connection region 254. During a fabrication process, the layered acoustic stack is laminated onto one side of interposer layer 250 (covering first and second connection regions 252, 254) and processed into a 2D array of transducer elements 256, such as set forth in FIG. 7. The joined transducer elements and flex circuit are then laminated onto the beam-forming electronics 258 under pressure using an adhesive such that the first connection region 252 (and transducer elements 256) is electrically joined to the first group of interconnect pads 260 associated with acoustic transmit and receive signals and such that the second connection region 254 is electrically joined to the second group of interconnect pads 262 associated with the signal I/O, power, and control functions. Beneficially, interposer 250 provides for the array of transducer elements to be built (components laminated, ground, cleaned, diced, etc.) without being attached to the surface of the beam-forming electronics 258, thereby limiting potential for damage to the beam-forming electronics. Additionally, interposer 250 provides for simultaneous connection of the beam-forming electronics 258 to the transducer elements 256 and to the signal I/O, power, and control connections in the interposer layer for easy connection to a system interconnect.

Therefore, according to an embodiment of the present invention, an ultrasound transducer includes an acoustic layer having an array of acoustic elements, a dematching layer coupled to the acoustic layer and having an acoustic impedance greater than an acoustic impedance of the acoustic layer, and an interposer layer coupled to the dematching layer and comprising a substrate and a plurality of conductive elements, with the interposer layer having an acoustic impedance lower than the acoustic impedance of the dematching layer. The ultrasound transducer also includes an integrated circuit coupled to the interposer layer and electrically connected to the array of acoustic elements through the dematching layer and the interposer layer.

According to another embodiment of the present invention, a method for manufacturing an ultrasound transducer includes the steps of providing an interposer layer, forming a plurality of vias in the interposer layer, adding an electrically conductive material within the vias, and coupling an acoustic layer to a dematching layer, the dematching layer having an acoustic impedance greater than an acoustic impedance of the acoustic layer and greater than an acoustic impedance of the interposer layer. The method also includes the steps of coupling the interposer layer to the dematching layer and coupling a beam forming electronics package to the interposer layer, the beam forming electronics package having a plurality of connection pads formed thereon and being electrically coupled to the acoustic layer by way of the interposer layer.

According to yet another embodiment of the present invention, an ultrasound transducer configured for use in an invasive probe includes an acoustic layer having an array of acoustic elements, a dematching layer coupled to the acoustic layer and having an acoustic impedance greater than an acoustic impedance of the acoustic layer, and beam forming electronics configured to send signals to the acoustic layer and receive signals from the acoustic layer and having a plurality of connection pads formed thereon. The ultrasound transducer also includes an interposer layer coupled to the dematching layer, the interposer layer further including an electrically non-conductive substrate having an acoustic impedance lower than the acoustic impedance of the dematching layer and having a plurality of vias formed therein, a first connection region configured to electrically connect the beam forming electronics to the acoustic layer and having a plurality of electrically conductive pathways extending through the plurality of vias, and a second connection region configured to electrically connect the beam forming electronics to system connections including at least one of a signal input/output connection, a power and control connection, and a ground and duplicate power connection.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound transducer comprising:
   an acoustic layer having an array of acoustic elements;
   a dematching layer coupled to the acoustic layer and having an acoustic impedance greater than an acoustic impedance of the acoustic layer;
   an interposer layer coupled to the dematching layer and comprising a substrate and a plurality of conductive elements, the interposer layer having an acoustic impedance lower than the acoustic impedance of the dematching layer; and
   an integrated circuit coupled to the interposer layer and electrically connected to the array of acoustic elements through the dematching layer and the interposer layer.

2. The ultrasound transducer of claim 1 wherein the interposer layer substrate comprises an electrically non-conductive substrate having a plurality of vias formed therein; and
   wherein the plurality of conductive elements comprises an electrically conductive path in each of the plurality of vias.

3. The ultrasound transducer of claim 2 wherein each of the substrate and the electrically conductive path has an acoustical impedance of less than approximately 10 MRayls.

4. The ultrasound transducer of claim 2 wherein the electrically conductive path comprises a silver epoxy filled in each of the plurality of vias.

5. The ultrasound transducer of claim 2 wherein the electrically conductive path comprises:
   an electrically conductive metal interconnect formed on the substrate and extending through each of the plurality of vias; and
   an electrically non-conductive epoxy filled-in over each metal interconnect and in a remainder of each of the plurality of vias.

6. The ultrasound transducer of claim 2 wherein the interposer layer further comprises a metal core embedded in the substrate, the metal core having a plurality of perforations formed therein; and
   wherein the plurality of vias extend through at least a portion of the plurality of perforations.

7. The ultrasound transducer of claim 2 wherein the interposer layer comprises:
   a first connection region configured to electrically connect the integrated circuit to the array of acoustic elements, the first connection region having the plurality of vias formed therein;
   a second connection region configured to electrically connect the integrated circuit to system connections including at least one of a signal input/output connection, a power and control connection, and a ground and duplicate power connection.

8. The ultrasound transducer of claim 7 wherein the second connection region comprises at least one of pad connections, trace connections, epoxy-filled single layer vias, and epoxy-filled through vias.

9. The ultrasound transducer of claim 2 wherein a pitch of the plurality of vias formed in the substrate matches a pitch of the array of acoustic elements.

10. The ultrasound transducer of claim 2 wherein the substrate comprises a multi-layer substrate including at least a top substrate layer and a bottom substrate layer having single layer vias formed therethrough, and wherein a pitch of the single layer vias in the top substrate layer differs from a pitch of the single layer vias in the bottom substrate layer.

11. The ultrasound transducer of claim 1 further comprising a lossy backing layer coupled to a back surface of the integrated circuit opposite the interposer layer.

12. A method for manufacturing an ultrasound transducer comprising:
    providing an interposer layer;
    forming a plurality of vias in the interposer layer;
    adding an electrically conductive material within the vias;
    coupling an acoustic layer to a dematching layer, the dematching layer having an acoustic impedance greater than an acoustic impedance of the acoustic layer and greater than an acoustic impedance of the interposer layer;
    coupling the interposer layer to the dematching layer; and
    coupling a beam forming electronics package to the interposer layer, the beam forming electronics package having a plurality of connection pads formed thereon and being electrically coupled to the acoustic layer by way of the interposer layer.

13. The method of claim 12 further comprising dicing the acoustic layer and the dematching layer to form an array of transducer elements.

14. The method of claim 13 wherein providing the interposer layer comprises providing an organic substrate; and
    wherein forming the plurality of vias comprises forming the plurality of vias in the organic substrate at a pitch equal to a pitch of the transducer elements.

15. The method of claim 13 wherein providing the interposer layer comprises providing a multi-layer organic substrate having at least a top substrate layer and a bottom substrate layer; and
    wherein forming the plurality of vias comprises:
    forming a plurality of vias in the bottom substrate layer at a pitch equal to a pitch of the plurality of connection pads on the beam forming electronics package; and
    forming a plurality of vias in the top substrate layer at a pitch equal to a pitch of the transducer elements.

16. The method of claim 13 wherein coupling the beam forming electronics package to the interposer layer comprises:
    coupling a first group of connection pads on the beam forming electronics package to a first connection region of the interposer layer, thereby electrically connecting the beam forming electronics package to the array of transducer elements; and
    coupling a second group of connection pads on the beam forming electronics package to a second connection region of the interposer layer, thereby electrically connecting the beam forming electronics package to system connections including at least one of a signal input/output connection, a power and control connection, and a ground and duplicate power connection.

17. The method of claim 16 wherein coupling the second group of connection pads to the second connection region comprises coupling the second group of connection pads to the second connection region through at least one of pad connections, trace connections, single layer vias, and through vias.

18. The method of claim 12 wherein adding the electrically conductive material within the vias comprises filling the vias with an epoxy having an acoustic impedance substantially similar to the acoustic impedance of the interposer layer.

19. The method of claim 12 wherein adding the electrically conductive material within the vias comprises:
    forming an electrically conductive metal interconnect within each of the vias; and filling a remaining portion of each of the vias with an electrically non-conductive epoxy having an acoustic impedance substantially similar to the acoustic impedance of the interposer layer.

20. An ultrasound transducer configured for use in an invasive probe, the ultrasound transducer comprising:

an acoustic layer having an array of acoustic elements;

a dematching layer coupled to the acoustic layer and having an acoustic impedance greater than an acoustic impedance of the acoustic layer;

beam forming electronics configured to send signals to the acoustic layer and receive signals from the acoustic layer and having a plurality of connection pads formed thereon; and an interposer layer coupled to the dematching layer, the interposer layer comprising:

an electrically non-conductive substrate having an acoustic impedance lower than the acoustic impedance of the dematching layer, the substrate having a plurality of vias formed therein;

a first connection region configured to electrically connect the beam forming electronics to the acoustic layer and having a plurality of electrically conductive pathways extending through the plurality of vias; and a second connection region configured to electrically connect the beam forming electronics to system connections including at pg,32 least one of a signal input/output connection, a power and control connection, and a ground and duplicate power connection.

21. The ultrasound transducer of claim 20 wherein the first connection region comprises:

a plurality of top surface connection pads; and a plurality of bottom surface connection pads;

wherein a pitch of the top surface connection pads matches a pitch of the array of acoustic elements, and wherein a pitch of the bottom surface connection pads matches a pitch of the beam forming electronics connection pads.

22. The ultrasound transducer of claim 20 wherein the second connection region comprises at least one of pad connections, trace connections, epoxy-filled single layer vias, and epoxy-filled through vias.

23. The ultrasound transducer of claim 20 wherein each of the substrate and the conductive pathways of the interposer layer have an acoustical impedance of less than approximately 10 MRayls.

24. The ultrasound transducer of claim 20 wherein the interposer layer substrate comprises a polyimide material, and wherein the filler material comprises silver epoxy.

25. The ultrasound transducer of claim 20 wherein the interposer layer further comprises a metal core embedded in the substrate and with the metal core having a plurality of perforations formed therein, and wherein the plurality of vias extend through at least a portion of the plurality of perforations.

* * * * *